United States Patent [19]
Jackson

[11] Patent Number: 5,931,803
[45] Date of Patent: Aug. 3, 1999

[54] EPOXY COATED TAMPON APPLICATOR HAVING A PIERCE-THROUGH FINGERGRIP

[75] Inventor: Dane R. Jackson, Bloomingdale, N.J.

[73] Assignee: Playtex Products, Inc., Westport, Conn.

[21] Appl. No.: 09/041,521

[22] Filed: Mar. 12, 1998

Related U.S. Application Data

[60] Provisional application No. 60/042,700, Apr. 4, 1997.

[51] Int. Cl.$^6$ .................................................. A61F 13/20
[52] U.S. Cl. ...................... 604/15; 427/558; 427/2.31; 493/229; 493/232
[58] Field of Search ....................... 604/11–18, 285–288, 604/904; 427/2.31, 293, 558; 493/229, 232

[56] References Cited

U.S. PATENT DOCUMENTS

| | | |
|---|---|---|
| 2,489,502 | 11/1949 | Ruth .......................................... 604/15 |
| 2,587,717 | 3/1952 | Fourness ................................... 604/15 |
| 3,139,886 | 7/1964 | Tallman et al. . |
| 3,390,671 | 7/1968 | Hildebrand . |
| 3,499,447 | 3/1970 | Mattes et al. . |
| 3,882,869 | 5/1975 | Hanke . |
| 4,146,453 | 3/1979 | Via . |
| 4,173,476 | 11/1979 | Smith et al. . |
| 4,319,974 | 3/1982 | Crivello . |
| 4,412,833 | 11/1983 | Wiegner et al. . |
| 4,508,531 | 4/1985 | Whitehead . |
| 4,599,401 | 7/1986 | Koleske . |
| 4,622,030 | 11/1986 | Sheldon et al. . |
| 4,977,199 | 12/1990 | Koleske et al. . |
| 4,981,881 | 1/1991 | Crivello et al. . |
| 5,102,772 | 4/1992 | Angelo et al. . |
| 5,346,468 | 9/1994 | Campion et al. . |
| 5,348,534 | 9/1994 | Tomaszewski et al. . |
| 5,709,652 | 1/1998 | Hagerty ..................................... 604/15 |

*Primary Examiner*—John G. Weiss
*Assistant Examiner*—Dennis Ruhl
*Attorney, Agent, or Firm*—Ohlandt, Greeley, Ruggiero & PErle, L.L.P.

[57] ABSTRACT

An applicator barrel is disclosed that is adapted for insertion into a body cavity. The applicator barrel has a pierce-through fingergrip area and an outer surface that is coated with an epoxy layer. Also disclosed is a method for forming such an applicator barrel, and tampon assemblies constructed with same.

25 Claims, 1 Drawing Sheet

EPOXY COATED TAMPON APPLICATOR HAVING A PIERCE-THROUGH FINGERGRIP

This application claims the benefit of U.S. Provisional application Ser. No. 60/042,700 filed Apr. 4, 1997.

BACKGROUND OF THE INVENTION

I. Field of the Invention

The invention relates to a cardboard tampon applicator. More particularly, the invention relates to a cardboard or paper laminate tampon applicator having a pierce-through fingergrip and an outer surface that is coated with an epoxy resin. The epoxy coated cardboard tampon applicator of the present invention can be formed inexpensively, without using volatile solvents, and will have a high degree of gloss for easier insertion, as well as improved cross-sectional circularity for reduced ejection force.

II. Description of the Prior Art

Tampon applicators are generally either a molded thermoplastic material, such as plastic, or a paper laminate, such as cardboard or paperboard.

Molded plastic can be used to form a tampon applicator. It is desired that such applicators have a generally circular cross-sectional shape. Maintaining this generally circular shape has been found to reduce the force needed to eject the tampon pledget from the applicator. Further, molded plastic applicators can be formed with a high degree of surface smoothness, which results in increased comfort during insertion of the tampon. However, plastic tampon applicators, unless certain expensive plastics are used, are neither water dispersible nor biodegradable. In an ecology minded society, biodegradability is desired.

To obtain biodegradability, a cardboard or paper laminate applicator is preferred since such applicators delaminate upon saturation with water, thereby facilitating biodegradation. However, a film laminated paper applicator is difficult to form with a perfectly circular cross-section, and the degree of circularity of the laminated paper applicator has been found to further degrade during the tube forming heating stage of the manufacturing process. Moreover, the fingergrip in such an applicator is important, but at the same time difficult to form with sufficient gripability.

Some commercially sold cardboard applicators have applied thereto either a separate film coat bonded by adhesive, or a liquid coating which then solidifies. A liquid wax coating is inexpensive to apply, and will not degrade the circularity of the tampon applicator during the manufacturing process. However, such liquid wax-coated tampon applicators do not have the desired surface smoothness and, therefore, do not provide the desired insertion comfort and reduced ejection force.

A polyester film coating, which has been used on commercially sold tampon applicators, has been found to shrink during the heating cycle of the applicator manufacturing process, causing the distortion of the applicator's shape thereby increasing the ejection force. A cellophane film also shrinks due to the evaporation of water absorbed from the adhesive used to apply it to the applicator. Further, cellophane is usually coated with a water resistant coating, such as nitrocellulose. Nitrocellulose coating of cellophane is expensive, and requires the use of a volatile organic solvent to apply the coating. The use of such a solvent requires special handling and disposal procedures, all of which further raise manufacturing costs.

Liquid coated paper laminate applicators are known in the art. For example, U.S. Pat. No. 4,412,833 to Weigner, et al. is directed to an applicator formed of a high-gloss paper that can be coated with a degradable, dispersible or water soluble polymer, such as a modified polyethylene, polypropylene, polyvinylidene chloride or polyvinyl alcohol. U.S. Pat. No. 4,508,531 to Whitehead, provides an applicator with a heat-sensitive coating, such as polyolefin (e.g., polyethylene or polypropylene) or a heat sensitive adhesive.

U.S. Pat. No. 4,622,030 to Shelton provides a thermoplastic coated paper tube. A film layer on a paper laminate tampon applicator is disclosed in U.S. Pat. No. 5,346,468 to Campion et al. This paper laminate tampon applicator has a thermoset polymer film layer adhered to the outer surface of the cardboard applicator. Preferably, this polymer film layer is a cellophane layer. However, there can be nitrocellulose over cellophane, and allegedly, in place of cellophane, a film layer of a thermoplastic polymer such as polyethylene, polyester, polypropylene, polycaprolactone or ethylene vinyl acetate.

Neither the liquid nor film coatings applied to the cardboard tampon applicators described above have permitted the combination of formation of the desired glossy finish, retention of applicator circularity, and sufficient biodegradability. Further, some prior art liquid coatings are more expensive, and require the use of organic solvents, leading to increased consumer cost.

There is a commercial tampon applicator by Paragon that has an epoxy coat. However, this applicator does not have the multiple puncture fingergrip of the present applicator and may not appreciate the significant circularity improvement provided by an epoxy coating.

The present invention is directed to applying a liquid coat on the surface of the paper laminate or cardboard applicator, and thereafter forming a multiple puncture fingergrip on the applicator. The formed applicator has the desired high gloss finish and maintains the improved degree of circularity of the applicator, while still permitting water dispersibility and biodegradability. The liquid coating of the present invention provides for the formation of the multiple puncture fingergrip, is inexpensive to apply, and does not require the use of organic solvents in the manufacturing process.

SUMMARY OF THE INVENTION

Against the forgoing background, it is a primary object of the present invention to provide a coated paper laminate or cardboard tampon applicator having a multiple puncture fingergrip that provides a high degree of insertion comfort.

It is another object of the invention to provide such an applicator that can maintain a preferred degree of circularity, leading to reduced ejection force.

It is yet another object of the present invention to provide such a coated applicator that can be inexpensively manufactured, without the use of organic solvents.

It is yet another object of the present invention to provide a water dispersible coated applicator where the coated layer will separate from the underlying substrate and the coated layer is readily water dispersible.

To accomplish the forgoing objects and advantages, the present invention, in brief summary, is a paper laminate or cardboard tampon applicator having a multiple puncture fingergrip that has an exterior surface coated with a thermoset, UV-curable epoxy resin. The epoxy resin can be applied to the applicator barrel, and even the plunger. Although described in terms of a tampon applicator, the present invention is equally useful in devices for the application of suppositories, creams, or the like to the vaginal area or other body cavities.

DETAILED DESCRIPTION OF THE PREFERRED EMBODIMENTS

The present invention provides an epoxy coating on a tampon applicator or similar device formed from a paper laminate or cardboard. The paper laminate applicator can be spirally or convolutely wound, as shown in the prior art. Basically, the applicator is formed by winding layers of paper or a paper-like material, such as cardboard, around a shaped mandrel, with each layer bonded, such as by glue or adhesive, to an adjacent layer.

Figure 1:
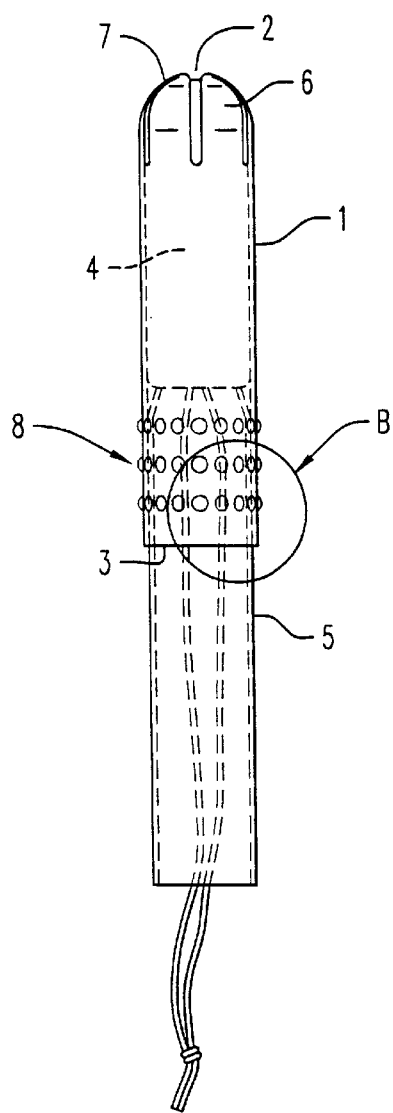
FIG. 1 is a side elevational view of a tampon applicator including the applicator barrel of the invention.

Referring to FIG. 1, a tampon applicator is shown. The tampon applicator includes an applicator barrel 1 having a forward end 2 and a rear end 3. The applicator barrel is formed of an epoxy coated paper-based product. Within applicator barrel 1 there is positioned a tampon pledget 4. A plunger 5 is adapted to slidingly engage rear end 3 of applicator barrel 1. The plunger 5 is adapted to contact the tampon pledget to expel tampon pledget 4 through forward end 2 of applicator barrel 1. Preferably, forward end 2 is constructed from a plurality of petals 6 collectively shaped to form a dome 7. The applicator barrel 1 is provided with a fingergrip area 8.

Figure 2:
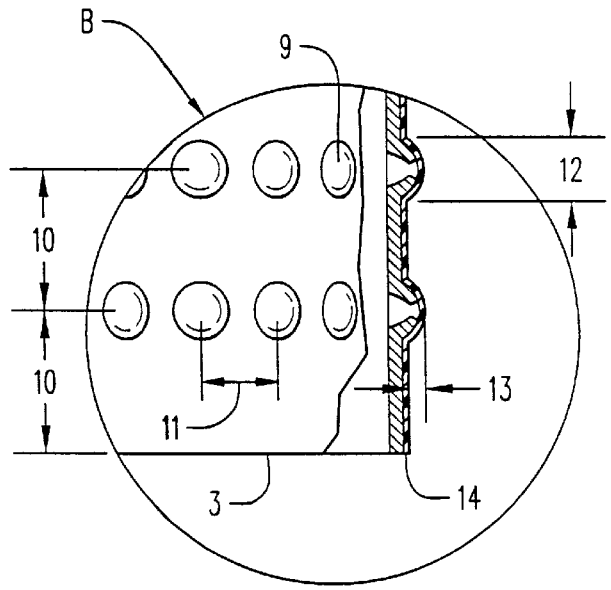
FIG. 2 is an enlarged view of region B of FIG. 1 showing an enlarged view of fingergrip area B of the applicator barrel shown in FIG. 1.

The details of fingergrip area 8 are shown in FIG. 2. Generally, fingergrip area 8 is provided proximal rear end 3 of applicator barrel 1 and is provided with texture by a plurality of outward-extending deformations 9. Although deformations 9 can be formed in any pattern, or randomly, within fingergrip area 8, it is convenient to form the deformations in rows positioned parallel to rear end 3 and spaced apart from each other by a row spacing distance 10, for example, by about 0.25 inches. Further, the deformations 9 in any given row will be spaced from each other by a deformation spacing distance 11, for example, by about 0.11 inches. Each deformation 9 can have a base deformation width 12 from about 0.0045 inches to about 0.080 inches, and an average-deformation height 13 about 0.016 inches. At the point of each deformation 9, the paper-based layer of the applicator barrel will be through pierced. The epoxy layer, identified in FIG. 2 as element 14, is not pierced and remains deformed but intact.

To form such a fingergrip, multiple deformations of the epoxy-coated laminate sheet are made from the interior side. The deformations puncture through the paper, but not the epoxy coating. The epoxy coating provides for the formation of superior fingergrips using this piercing technology since it permits the ready piercing or puncturing of the entire paper, but not the through-piercing of the coating. In contrast, polyester coatings are so tough that the sheets cannot be easily deformed and optimum deformation height cannot be easily achieved. Thus, the epoxy coated applicator of the present invention provides superior fingergrip compared to polyester coated applicators when the piercing technology is employed.

The liquid coating of the present application is an epoxy resin that is solidified by ultraviolet (UV) radiation. The present cardboard applicator provides for the application of the epoxy resin to a first side of a first sheet that will form the outer surface of the cardboard applicator. Thereafter, the coated first sheet is adhered to a second sheet to form a laminated structure that is, in turn, formed into the body of the tampon applicator. The first surface will form the exterior or outer surface of the formed cardboard applicator.

In the present coating, the epoxy resin includes a multifunctional epoxide base resin and a photoinitiator. Preferably, the epoxy resin will also include a reactive diluent, a plasticizer and a leveling agent. The reactive diluent is used to lower the viscosity of the resin formulation but will crosslink with the epoxy upon curing. The leveling agent is used to increase the flow and leveling of the liquid epoxy on the paper so that a smooth surface is formed.

In the preferred epoxy resin, the multifunctional epoxide is about 50 to about 95 wt. % of the resin. The combination of the photoinitiator and carrier is present in an amount about 1 to about 10 wt. %. The reactive diluent is about 5 to about 40 wt. % of the resin, the plasticizer is about zero to about 5 wt. % of the resin, and the leveling agent is present in an amount of zero to about 5 wt. %.

The epoxy resin preferably is a U.V. photopolymerizable cycloaliphatic epoxide. The photoinitiator preferably is a triaryl sulfonium salt. The reactive diluent preferably is a polycaprolactone polyol. The plasticizer preferably is propylene carbonate. The leveling agent preferably is a polyether-modified polydimethylsiloxane.

The paper to which the epoxy resin is applied is, preferably, one that is smooth but is not highly calendered to an extremely smooth finish. One example of a suitable paper is 25 pound MC RHI-liner 23/code 342-2503 sold by Rhinelander.

The epoxy resin is applied onto the first surface as a liquid by any conventional coating application. The resin is then solidified by exposure to an amount of ultraviolet (UV) light or radiation sufficient to initiate crosslinking in the epoxy resin. This process forms a high gloss, hardened epoxy coat. Thereafter, an aqueous adhesive is applied to a second side of the first sheet. Under nip roll pressure, the first sheet is bonded to the second sheet. The second sheet, in turn may be bonded to a third or more sheet to form the laminated structure. The laminate structure is then cut into small substrates or blanks. The substrates or blanks are subsequently wound around a mandrel and heated to form the applicator. Either the blanks or the formed applicators are pierced to form the fingergrip area. In a preferred applicator, the applicator is convolutely wound.

The epoxy resin is applied to the first sheet in an amount at least about 2 pounds per ream. A ream contains approximately 3,000 square feet of paper. Preferably, the epoxy resin will be applied in an amount of 2 to 6 pounds per ream. The application of a greater amount of the epoxy resin leads to a smoother and glossier finish.

The specular gloss of the finish can be measured using the procedures of ASTM test method number D523, the testing procedure of which is incorporated herein by reference. Using the 60 degree incidence option of ASTM test method number D523-89, the glossiness of epoxy coated applicators of the present invention (at coating levels of 2 pounds per ream and 4 pounds per ream) were compared to the glossiness of a conventional wax-coated applicator. Because the test procedure requires that a flat surface be measured, the tests were conducted using coated laminate blanks, rather than coated applicator barrels. The results achieved (95% confidence level) are as follows:

| SPECULAR GLOSS (unitless) | | | |
|---|---|---|---|
|  | Wax Coated Paper | Epoxy Coated Paper (2 lbs/ream) | Epoxy Coated Paper (4 lbs./ream) |
| Average | 28.1 | 33.3 | 57.6 |
| Std. Deviation | 1.5 | 2.6 | 5.7 |
| Number | 6 | 6 | 6 |

It has been found that the heat needed for formation of the applicator causes shrinkage of the known nitrocellulose over cellophane film and polyester film coated cardboard applicators. However, the epoxy resin coating does not shrink. Thus, the epoxy coated cardboard applicator will not cause distortions in the cross-section of the applicator and the applicator petals. This improved degree of circularity has been found to reduce the amount of force required to eject the pledget from the applicator, and prevent the jamming of the plunger in the applicator barrel.

The degree of circularity can be defined by optically measuring the major and minor diameters of the applicator and determining the perimeter thereof. The major diameter is then compared to the diameter of a perfect circle having the same perimeter as the measured applicator. The result is expressed in terms of % Ovality, which is defined as follows:

$$\% \text{ Ovality} = \left(\left(\frac{\text{Major diameter of the applicator}}{\text{Diameter of a perfect circle of the same perimeter}}\right) - 1\right) \times 100$$

Epoxy-coated applicators of the present invention were compared to polyester film coated applicators with the following results:

|  | Epoxy Coated | Polyester Film Coated |
|---|---|---|
| % Ovality | 1.58 | 2.75 |
| Std. Dev. | 0.008 | 0.944 |
| Number | 20 | 50 |

As is demonstrated by the foregoing test data, the epoxy coated applicators of the present invention have a statistically ($\geq 99\%$ confidence level) lower degree of ovality (are more circular) than polyester film coated applicators.

In addition, the epoxy coating is more water dispersible than prior polyester film coatings and nitrocellulose over cellophane coatings. Therefore, when flushed, the epoxy coating will disperse with only mild agitation, and will not separate from the applicator as a self-standing film. In contrast to polyester, epoxy will not delaminate from the applicator paper laminate. Moreover, the epoxy coating allows for the formation of an improved multiple puncture fingergrip.

Furthermore, the resultant coated tampon applicator has a smooth, hydrophobic surface that provides for comfortable insertion of the applicator. It also is believed that the epoxy coated applicator has a superior appearance and feel. Moreover, the epoxy coat on the multiple puncture fingergrip of the present applicator provides a superior fingergrip surface.

When the plunger is also coated with epoxy, the ejection properties of the tampon are further improved. Because the epoxy coating is very hydrophobic, it resists the swelling and/or raising of pulp fibers on the surface of the plunger in situations where the surface gets wet from, for example, wet hands or menses. A reduced swelling of the plunger avoids ejection force problems due to barrel/plunger fit or function interference.

In a blind consumer test, 202 women were given 10 super absorbency tampons with the commercially available liquid wax coated cardboard applicators and 10 super absorbency tampons with the liquid epoxy coated cardboard applicators. Each applicator had multiple punctures in the fingergrip, and each was identical except for the coating. After each women used the tampons, she was asked which applicator she preferred for various applicator attributes. For the women who had a preference, the results are tabulated below.

| Applicator Attributes | Prefer Epoxy Coating | Prefer Wax Coating |
|---|---|---|
| Easy to insert (Insertion) | 70% | 30% |
| Easy to eject from applicator | 68% | 32% |
| Feel of the applicator | 83% | 17% |
| Appearance of the applicator | 75% | 25% |
| The applicator | 75% | 25% |

Thus, consumer testing confirms that in comparison to wax coated applicators, the epoxy coated applicator is easier to insert, has decreased ejection force, and provides improved applicator feel and appearance.

While a preferred embodiment in accordance with the present invention has been shown and described, it is to be clearly understood that the same is susceptible to numerous changes apparent to one of ordinary skill in the art. Therefore, the present invention should not be deemed to be limited to the details shown and described above, and should be considered to include all changes and modifications that come within the scope of the appended claims.

What is claimed is:

1. A tampon assembly comprising:
    an applicator barrel having a forward end and a rear end, said applicator barrel being formed of a paper-based product having an outer surface coated with a cured layer of UV-curable epoxy resin, said outer surface having a fingergrip area adjacent said rear end, said fingergrip area having a plurality of outward extending deformations that rupture said paper-based product of said applicator barrel but do not penetrate through said cured layer.

2. The tampon assembly of claim 1, wherein said paper-based product is selected from the group consisting of paper laminate and cardboard.

3. The tampon assembly of claim 1, wherein said epoxy resin includes a multifunctional epoxide base resin and a photoinitiator.

4. The tampon assembly of claim 3, wherein said epoxy resin further comprises at least one additional component selected from the group consisting of a reactive diluent, a plasticizer, a leveling agent and a carrier.

5. The tampon assembly of claim 4, wherein said epoxy resin comprises;
    about 50 wt. % to about 95 wt. % of said multifunctional epoxide base resin;
    about 1 wt. % to about 10 wt. % of a combination of said photoinitiator and carrier;
    about 5 wt. % to about 40 wt. % of said diluent;
    about zero to about 5 wt. % of said plasticizer; and
    about zero to about 5 wt. % of said leveling agent.

6. The tampon assembly of claim 5, wherein said multifunctional epoxide base resin is a cycloaliphatic epoxide, said photoinitiator is a triaryl sulfonium salt, said diluent is polycaprolactone polyol, said plasticizer is propylene carbonate, and said leveling agent is polyether-modified polydimethylsiloxane.

7. The tampon assembly of claim 1, wherein said plurality of deformations that form said fingergrip area are arranged in a plurality of spaced rows substantially parallel to said rear end.

8. The tampon assembly of claim 7, wherein said plurality of spaced apart rows are spaced apart by about 0.25 inches, and each of said plurality of deformations in each of said plurality of rows are spaced apart by about 0.11 inches.

9. The tampon assembly of claim 7, wherein each of said plurality of deformations has an average base width from about 0.0045 inches to about 0.080 inches, and an average height of about 0.016 inches.

10. The tampon assembly of claim 1, wherein an outer surface of said plunger is provided with a second cured layer of UV-curable epoxy resin.

11. An applicator barrel for insertion into a body cavity, the applicator barrel being formed of a paper-based product, an outer surface of said applicator barrel being coated with a cured layer of UV-curable epoxy resin, said outer surface having a fingergrip area formed of a plurality of outward extending deformations that rupture the paper-based product of said applicator barrel but do not penetrate through said cured layer.

12. The applicator barrel of claim 11, wherein said paper-based product is selected from the group consisting of paper laminate and cardboard.

13. The applicator barrel of claim 12, wherein said epoxy resin includes a multifunctional epoxide base resin and a photoinitiator.

14. The applicator barrel of claim 13, wherein said epoxy resin further comprises at least one additional component selected from the group consisting of a reactive diluent, a plasticizer and a leveling agent and a carrier.

15. The applicator barrel of claim 14, wherein said epoxy resin comprises:

about 50 wt. % to about 95 wt. % of said multifunctional epoxide base;

about 1 wt. % to about 10 wt. % of a combination of said photoinitiator and carrier;

about 5 wt. % to about 40 wt. % of said diluent; about zero to about 5 wt. % of said plasticizer; and about zero to about 5 wt. % of said leveling agent.

16. The applicator barrel of claim 15, wherein said multifunctional epoxide base resin is a cycloaliphatic epoxide, said photoinitiator is a triaryl sulfonium salt, said diluent is polycaprolactone polyol, said plasticizer is propylene carbonate, and said leveling agent is polyether-modified polydimethylsiloxane.

17. The applicator barrel of claim 16, wherein said plurality of deformations that form said fingergrip area are arranged in a plurality of spaced rows substantially parallel to said rear end.

18. The applicator barrel of claim 17, wherein said plurality of spaced rows are spaced apart by about 0.25 inches, and each of said plurality of deformations in each of said plurality of rows are spaced apart by about 0.11 inches.

19. The applicator barrel of claim 18, wherein each of said plurality of deformations has an average base width from about 0.0045 inches to about 0.080 inches, and an average height of about 0.016 inches.

20. A method of forming an applicator barrel including a fingergrip area, said applicator barrel being adapted for insertion into a body cavity, said method comprising:

forming a blank from a paper-based product;

coating a first side of said blank with UV-curable epoxy resin;

curing said epoxy resin by exposing the coated first side to UV light or radiation to form a cured layer;

winding said blank to form an applicator barrel on which said first side coated with said cured layer forms an exterior surface; and piercing said paper based material a plurality of times from inside said barrel through said first side to form a plurality of outward extending deformations that rupture said paper based product of said applicator barrel but do not penetrate through said cured layer, in an area corresponding to the fingergrip area.

21. The method of claim 20, wherein said blank is convolutely wound.

22. The method of claim 20, wherein said blank is spirally wound.

23. The method of claim 20, wherein said paper-based product is selected from the group consisting of paper laminate and cardboard.

24. The method of claim 20, wherein said epoxy resin is applied to said first side of said blank in an amount of at least about 2 pounds per 3000 ft$^2$ of paper-based product.

25. The method of claim 24, wherein said amount is from about 2 to about 6 pounds per 3000 ft$^2$ of paper-based product.

* * * * *